United States Patent
Li et al.

[19]

[11] Patent Number: 5,981,958
[45] Date of Patent: Nov. 9, 1999

[54] METHOD AND APPARATUS FOR DETECTING PATHOLOGICAL AND PHYSIOLOGICAL CHANGE IN PLANTS

[76] Inventors: Ning Li, 309 SW. 9th St., Apt. 5, Corvallis, Oreg. 97333; Gerald E. Edwards, SW. 1030 Monta Vista, Pullman, Wash. 99163; Larry S. Daley, 1850 NW. Arthur Cir., Corvallis, Oreg. 97330

[21] Appl. No.: 08/739,315

[22] Filed: Oct. 29, 1996

Related U.S. Application Data

[60] Provisional application No. 60/010,025, Jan. 16, 1996.

[51] Int. Cl.⁶ .................................................. G01N 21/64
[52] U.S. Cl. ........................................ 250/459.1; 356/317
[58] Field of Search ............................. 250/458.1, 459.1; 356/317

[56] References Cited

U.S. PATENT DOCUMENTS

| | | |
|---|---|---|
| 4,224,304 | 9/1980 | Sawai et al. . |
| 4,407,008 | 9/1983 | Schmidt et al. . |
| 4,650,336 | 3/1987 | Moll ........................................ 356/317 |
| 5,130,545 | 7/1992 | Lussier ................................. 250/459.1 |
| 5,239,171 | 8/1993 | Takabayashi et al. . |
| 5,329,352 | 7/1994 | Jacobsen . |
| 5,337,139 | 8/1994 | Shirasawa . |
| 5,381,224 | 1/1995 | Dixon et al. . |
| 5,469,251 | 11/1995 | Kosaka et al. . |
| 5,658,418 | 8/1997 | Coronel et al. . |

FOREIGN PATENT DOCUMENTS

| | | | |
|---|---|---|---|
| 33 03 510 | 7/1983 | Germany ............................. | 250/458.1 |
| 87/06698 | 11/1987 | WIPO ................................. | 250/458.1 |

OTHER PUBLICATIONS

Omasa et al., "Image Analysis of Chlorophyll Fluorescence Transients for Diagnosing the Photosanthetic System of Attached Leaves", *Plant Physiol.* vol. 84, pp. 748–752 (1987).

Daley, P.F., "Chlorophyll Fluorescence Analysis and Imaging in Plant Stress and Disease", *Canadian J. Plant Pathol.*, vol. 17 (2), pp. 167–173 (1995).

Li Ning, et al., "Construction of an Imaging Visible Spectrophotometer and Its Application to Plant Sciences," *Spectroscopy* 9 (7), Sep. 1994, pp. 41–48.

*Primary Examiner*—Constantine Hannaher
*Attorney, Agent, or Firm*—Klarquist Sparkman Campbell Leigh & Whinston LLP

[57] ABSTRACT

An imaging fluorometer is described comprising a source of electromagnetic radiation, optical components to direct the radiation, excitation and emission filters, and an imaging device. The fluorometer is used to obtain images of the fluorescence emitted by illuminated arrays of photosynthetic components, such as those found in leaves. These fluorescence images, in turn, are used to construct an image of the photosynthetic efficiency of the array. Because efficiency in plants depends on the physiological state of the leaf, the fluorometer affords a method for the sensitive and rapid characterization of freeze damage, herbicide damage, and disease damage to plants. Moreover, the fluorometer may be used in robotic applications, as well as for remote sensing from a location distant from the plant.

12 Claims, 8 Drawing Sheets

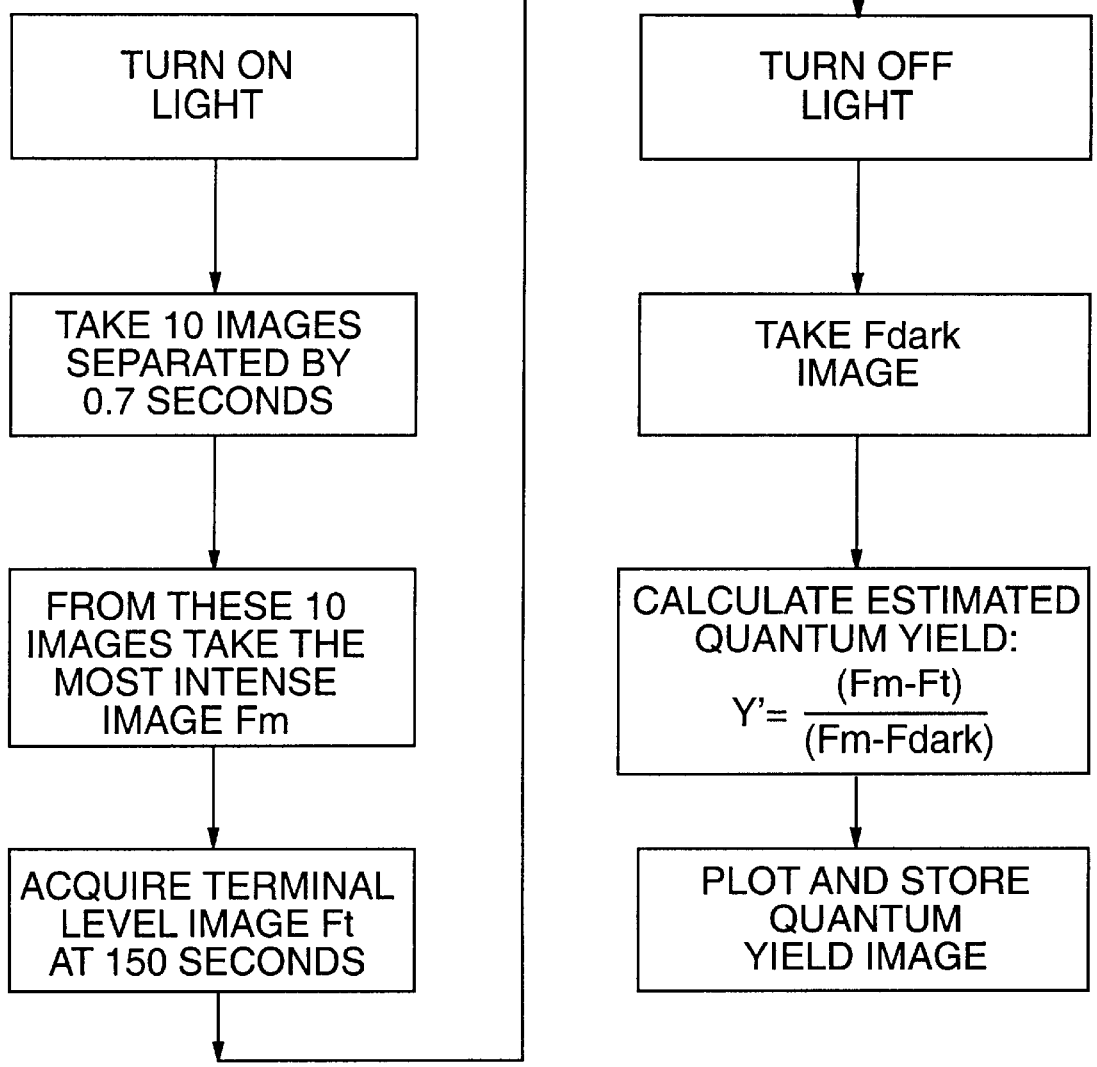

METHOD AND APPARATUS FOR DETECTING PATHOLOGICAL AND PHYSIOLOGICAL CHANGE IN PLANTS

This application claims the benefit of U.S. Provisional Application No. 60/010,025, filed Jan. 6, 1996.

TECHNICAL FIELD

This invention relates to devices used to measure fluorescence and more specifically to a device used to construct images based on the fluorescence emitted by plants.

BACKGROUND OF THE INVENTION

Photosynthesis

Plant leaves are the site of photosynthesis, a process by which the energy in sunlight is harnessed and used to generate foodstuffs. As sunlight is gathered, water is split, with its hydrogens used to reduce certain chemical compounds and its oxygen used to form $O_2$. The reduction of chemical compounds by the light-driven mechanisms of photosynthesis is termed the "light reaction"; the use of these reduced compounds to fix $CO_2$ into foodstuffs is termed the "dark reaction" (Taiz, L. and Zeiger, E., *Plant Physiology*, Benjamin/Cummings Pub. Co., Inc., Redwood City, Calif., 1991, Chap. 8–10, p. 177).

The light and dark "reactions" are not single steps, but instead comprise several complex series of reactions, each involving electron transfer (Taiz and Zeiger, 1991). The light reaction is divided into two "photosystems." Photosystem II ($PS_{II}$) comprises the reactions leading to the splitting of water and the release of oxygen. Photosystem I ($PS_I$) comprises the reactions leading to the reduction of $NADP^+$ (nicotinamide adenine dinucleotide phosphate) to NADPH, a compound which provides energy used in the dark reaction (Taiz and Zeiger, 1991).

Plant Fluorescence

Chlorophylls and certain other molecules involved in photosynthesis absorb visible light, "funneling" the absorbed energy in the form of free electrons to reaction centers (RCs) that are parts of the two photosystems (Taiz and Zeiger, 1991; Bolhar-Nordenkampf, H. R. and Oquist, G., "Chlorophyll Fluorescence as a Tool in Photosynthesis Research," in *Photosynthesis and Production in a Changing Environment*, a Field and Laboratory Manual, Hall, D. O., Scurlock, J. M. O., Bolhar-Nordenkampf, H. R., Leegood, R. C. and Long, S. P. Eds., Chapman and Hall, London, 1993, Chap. 12, p. 193). When the RCs are maximally available (open), about 97% of the absorbed light energy is productively used for photochemical reactions leading to the production of foodstuffs, about 2.5% is "lost" as heat, and about 0.5% is re-emitted at longer wavelengths as fluorescence (Bolhar-Nordenkampf and Oquist, 1993). When the RCs are not available (closed), about 90–95% of absorbed light energy is lost as heat, and about 2.5–5% is re-emitted as fluorescence (Bolhar-Nordenkampf and Oquist, 1993).

Fluorescence from photosynthetic systems is thus tightly coupled to the availability of RCs, as is especially evident when dark-adapted systems are first illuminated. When photosynthetic systems are initially illuminated, fluorescence is low because most RCs are open. However, with continued illumination, fluorescence increases and then varies with time in a characteristic manner as the RCs are recruited into use and the light energy is employed to Dower various reactions (Bolhar-Nordenkampf and Oquist, 1993). If the illumination is constant, a plot of fluorescence versus time will have a characteristic shape known as the Kautsky curve (Kautsky, H. and Hirsch, A., *Biochem. Zeitschrift* 274, 423, 1934). Important features of this curve have been designated by the upper-case letters OIDPSMT, corresponding to Origin of curve or initial fluorescence, Initial rise, Dip, Peak, down Slope (or quasi-steady-state) between-primary (P) and secondary (M) maxima, and Terminal level, respectively (Lavorel, J. and Etienne, A. L., "In Vivo Chlorophyll Fluorescence," in Topics in *Photosynthesis,* 2, Barber, J. Ed., Elsevier, Amsterdam, 1977, p. 203).

OIDPSMT transients reflect the availability of RCs and the rate of electron flow through the electron transport chain of the light reaction (Mawson, B. T., Morrissey, P. J., Gomez, A. and Melis, A., *Plant Cell Physiol.* 35, 341, 1994; Papageorgiou, G., "Chlorophyll Fluorescence: an Intrinsic Probe of Photosynthesis," in *Bioenergetics of Photosynthesis*, Govindjee [no first initial] Ed., Academic Press, New York, 1975, p. 319.; Powles, S. B., *Ann. Rev. Plant Physiol.* 35:14, 1984; Edner, H., Johansson, J., Svanberg, S. and Wallinder, E., *Applied Optics* 33, 2471, 1994; Methy, M., Olioso, A. and Trabaud, L., *Remote Sens. Environ.* 47, 42, 1994). When a dark-adapted system is illuminated, chlorophyll antenna in light-harvesting complex (LHC) II and $PS_{II}$ quickly begin funneling light energy in the form of free electrons to the RCs of $PS_{II}$, closing RCs and increasing fluorescence within picoseconds (transient O). However, free electrons within the RCs are transferred within milliseconds to electron acceptor $Q_A$ (transient I) and electron acceptor $Q_B$ (transient D), re-opening the RCs and decreasing the fluorescence. $Q_A$ and $Q_B$ are saturated within a millisecond, again closing RCs and increasing fluorescence, which reaches a maximum and peaks within about 0.5–2 seconds (transient P). A minimum (transient S) and second maximum (transient S) occur as electrons are transferred to LHCI and $PS_I$, which then saturate. By this time, the dark reactions of photosynthesis begin demanding reducing "power," which re-opens the RCs and reduces fluorescence to background levels after a hundred to several hundred seconds (transient T).

Practical Implications of Plant Fluorescence

The time dependence of plant fluorescence manifest in the OIDPSMT curve can be used to detect pathological and physiological changes in plants and differences between plants. For example, the OIDPSMT curve depends on the physiological condition and type of plant, the structure and potential for activity of the photosynthetic apparatus, the demands of the dark reaction, the health of the leaf, and the plant's adaptation to environmental conditions (Tecsi, L. I., Maule, A. J., Smith, A. M and Leegood, R. C., *Plant J.* 5, 837, 1994; Havaux, M. and Lannoye, R., *Photosynthetica* 18, 117, 1984; Omasa, K., Shimazaki, K., Aiga, L., Larcher, W. and Onoe, M., *Plant Physiol.* 84, 748, 1987; Bolhar-Nordenkampf, H. R. and Lechner, E. G., "Winter Stress and Chlorophyll Fluorescence in Norway Spruce (*Picea abies* (L.) Karst)," in *Applications of Chlorophyll Fluorescence*, Lichtenthaler, H. K. Ed., Kluwer Academic Publ., Dordretcht, Holland, 1988, p. 173; Ghirardi, M. L. and Melis, A., *Biochem. Biophys. Acta* 932, 130, 1988; Daley, P. F., Raschke, K., Ball, J. T. and Berry, J. A., *Plant Physiol.* 90, 1233, 1989; Osmond, C. B., Berry, J. A., Balachandra, S., Buchen-Osmond, C., Daley, P. E, and Hodgson, R. A., *Bot. Acta* 103, 226, 1990). Moreover, fluorescence varies across the face of the leaf in ways diagnostic of leaf function (Daley et al., 1989).

At room temperature, $PS_{II}$ is the major and most variable source of fluorescence (Bolhar-Nordenkampf and Oquist, 1993). Fluorescence signals from $PS_{II}$ are sensitive to environmental stresses, such as high temperature, chilling, freezing, drought, and excess radiation.(Smillie, R. M., "The Useful Chloroplast: a New Approach for Investigating Chilling Stress in Plants," in *Low Temperature Stress in Crop Plants*, Lyons, J. M., Graham, D. and Raison, J. K. Eds., Academic Press, New York, 1979, p. 187; Havaux and Lannoye, 1984; Powles, 1984).

Although fluorescence reports directly on the light reaction, it can also be used to assay the dark reaction in plants with C-4 metabolism (Ning, L., Ozanich, R., Daley, L. S. and Callis, J. B., *Spectroscopy* 9(7), 41, 1994), such as corn (*Zea mays* L.). This is because in C-4 plants most electron flow through $PS_{II}$ is used, via $PS_I$, to make NADPH for carbon fixation in the dark reaction. Fluorescence from $PS_{II}$ is thus closely correlated with the quantum yield of $CO_2$ fixation (Edwards, G. E. and Baker, N. R., *Photosynthesis Research* 37, 89, 1993).

Thus, imaging of plant fluorescence could be a rich source of information on plant pathology and physiology, particularly for the agricultural industry. However, a need exists for simple methods of accessing and interpreting the information contained in plant fluorescence.

Quantum Yield

One simple method of obtaining information about plant pathology and physiology from plant fluorescence is to compute the quantum yield or maximum intrinsic efficiency, Y, of $PS_{II}$, which is given by the ratio (Bolhar-Nordenkampf and Oquist, 1993):

$$Y=(F_P-F_O)/F_P \tag{1}$$

Here $F_P$ is the peak fluorescence and $F_O$ is the origin fluorescence in the Kautsky curve.

Unfortunately, Y is not a perfect measure of photochemical efficiency, because stress can lead to restrictions on electron flow or carbon fixation not manifest in $F_O$ or $F_P$. Moreover, measurement of $F_O$ is difficult, because $F_O$ occurs over a very short time period. In addition, measurement of $F_P$ must be precisely timed to capture the peak fluorescence, a time that varies with plant pathology and physiology. Thus, a need exists for alternatives to Eq. 1 that will more conveniently and accurately measure photochemical efficiency.

Robotic Agriculture

Photosynthetic efficiency is of major economic interest because it is directly coupled to agricultural productivity. The agricultural industry attempts to maximize photosynthetic efficiency by providing plants with appropriately timed inputs, such as pesticides, fertilizer, and water.

Currently, agricultural pesticide, fertilizer, and irrigation schedules are determined by manual field scouting, in which a trained observer interprets leaf signals and other indicators of plant health. Field scouting, supplemented by laboratory analysis, is an expensive and time-consuming process. Moreover, following scouting, agricultural inputs are applied uniformly on entire fields, leading to the excess use and runoff of pesticides, fertilizer, and water.

As an alternative, robots could be used to supply an individual mix of agricultural inputs to each plant in every part of a field. Already, devices exist to locate and spray individual weeds. Much more could be done in the future: pesticides could be rapidly applied only to afflicted plants, killing pests before they spread, or fertilizer and water could be supplied only as required by each plant.

However, to provide inputs to individual plants, a robot must receive and process information on the condition of individual plants. Therefore, a need exists for simple data inputs to help robotic agriculture.

Futures Market

In the volatile agricultural futures market, information on crop conditions is used to help predict the future prices of agricultural commodities. Prices vary as conditions vary; for example, futures prices for citrus may rise following frost damage to the citrus crop. When crop information is delayed or incomplete, market instabilities can arise. Therefore, a need exists for rapid determination of crop conditions, particularly conditions relating to harvest size.

Biomolecular Electronics

Biomolecular electronics is the use of biological molecules in the construction of electronic devices. Photosynthetic components are potentially valuable components of biomolecular electronic devices because they are essentially microscopic photoelectronic devices. As photons are absorbed by a photosynthetic system, electron transfer reactions are initiated that result in a unidirectional, spatial separation of charges across the photosynthetic membrane. In essence, this separation can be regarded as electron movement through an insulating medium, controlled at the molecular level (Boxer, S. G., Stocker, J., Franzen, S., and Salafsky, J., "Re-engineering photosynthetic reaction centers," in *Molecular Electronic Science* and *Technology*, Aviram, A. Ed., Amer. Inst. Physics, New York, 1992, pp. 226–236).

Two potential electronic uses of photosynthetic systems are: a) coupling of chloroplast components to electronic systems (Greenbaum, E., *J. Phys. Chem.* 94, 6151, 1990; Greenbaum, E., *J. Phys. Chem.* 96, 514, 1992; Greenbaum, E., "Biomolecular electronics and applications," in *Molecular Biology and Biotechnology: a Comprehensive Desk Reference*, Meyers, R. M. Ed., VCH Publishers Inc., New York, 1995, pp. 98–103.), and b) re-engineering of photosynthetic reaction systems for bioelectronic applications (Boxer et al., 1992). However, the quality of the biomolecular electronic device built around photosynthetic components will depend on the efficiency of the photosynthetic components. Because photosynthetic materials differ greatly in efficiency, a need exists for a method to screen photosynthetic systems for their efficiency before they can be effectively exploited in biomolecular electronics.

SUMMARY OF THE INVENTION

In view of the above, an object of the present invention is to provide a simple method to extract information on plant physiology from plant fluorescence.

Another object of the invention is to provide information on plant physiology unavailable from the standard quantum yield of photosynthesis.

Yet another object of the invention is to provide a rapid and economic alternative to manual field scouting.

Yet another object of the invention is to provide image data to guide robotic agriculture.

Yet another object of the invention is to provide a method of screening photosynthetic components for their efficiency.

The invention achieves one or more of these and other objects [and advantages both individually and collectively,] as will become apparent with reference to the accompanying description, drawings, and claims.

The present invention provides an imaging fluorometer comprising a source of electromagnetic radiation, optical components to direct the radiation, excitation and emission filters, and an imaging-device. Radiation from the radiation source is used to excite fluorescence from a dark-adapted sample containing photosynthetic components. This fluorescence is collected by the imaging device as a function of time and position within the sample. Excitation and emission filters limit the intensity and wavelengths of radiation incident on the sample and imaging device, respectively.

Fluorescence data are used to compute an effective quantum yield, Y', for photosynthetic efficiency based on improvements to Eq. 1. The peak fluorescence $F_P$ is approximated by the maximum measured fluorescence, obviating the need to know the precise time at which the peak fluorescence occurs. The initial fluorescence $F_O$ is approximated by the terminal fluorescence, obviating the need to make picosecond measurements. Finally, both quantities are corrected for errors introduced by the imaging device.

Determination of Y' is rapid, typically taking about 2.5 minutes. The limiting determinant of the acquisition time is the time required for the fluorescence to attain its terminal value, $F_t$.

The invention also provides a method for detecting pathological and physiological differences in plants. Values of Y' are shown to reflect freeze damage, herbicide and toxin damage, and disease damage. Thus, to detect differences, measured values of Y' can be compared with standard values obtained from healthy areas of the plant image or from control plants. Based on the comparison, agricultural inputs such as pesticides, fertilizer, and water can be applied as required, on a plant-by-plant basis.

The invention can be used Lo measure the light, heat or cold tolerance or water status of or mechanical, biological or other damage to a leaf and thus guide the adjustment of plant cultural conditions accordingly by use of such techniques as shading, heating, plant spacing, intercropping other crops, watering, installing windbreaks, insecticide applications and the like.

The invention can employ automated image pattern interpretation to diagnose, through artificial intelligence methods, the nature of harm to a leaf and thus determine the appropriate agricultural response.

The invention also provides methods for automating agriculture. The fluorometer can be used in robotic agriculture by incorporating it into a device that can move to a plant, make a determination about its needs, and then apply an appropriate input. The fluorometer can also be used as a remote sensor, operating at a distance to look at different plants, or at collections of plants, without moving.

The invention is useful in the field of bioelectronics since reaction centers, photosynthetic antennas arrays, and chlorophyll protein complexes differ with plant source and physiological state of the plant. Instruments according to the present invention can be used to select the most appropriate plant components and material from among the many hundred thousands of plant species, millions of plant germplasm variations and the many million of photosynthetic variants/species combinations for each in vitro bioelectronic circuit and for each in vivo bioelectronic use in bioengineered living organisms. There are numerous applications for such bioelectronic components including devices for light detection and solar driven photochemistry using bioelectronic circuit boards, and devices capable of: (a) very efficient use of light to generate electricity directly, (b) producing hydrogen and oxygen from water to fuel motors, (c) producing fresh water from salt water by first producing separately hydrogen and oxygen, and then recombining them in an area free of salt thus generating pure water and recovering much of the solar energy invested in separating the gases, (d) being components inserted or bioengineered into animals to make them capable of deriving part or all of their carbon and energy sources from sunlight and atmospheric carbon dioxide. In each case the present invention can be used to select the most appropriate plant source of the bioelectric component for the desired application.

BRIEF DESCRIPTION OF THE DRAWINGS

In order that the invention may be clearly understood, it will now be described, by way of examples, with reference to the following figures:

FIG. 3 is a flow chart showing a preferred protocol for measuring the estimated quantum yield, Y'.

FIG. 6a shows effects 15 minutes after 12 drops of DCMU solution were placed on a leaf; FIG. 6b shows effects 12 hours after allowing the petiole of the leaf to take un the DCMU solution.

DETAILED DESCRIPTION

Apparatus

Figure 1:
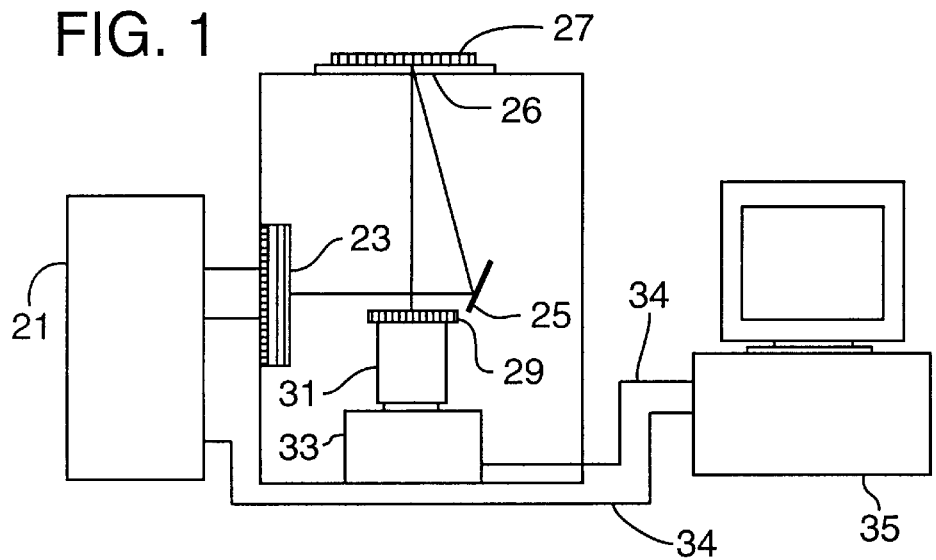
FIG. 1 is a schematic view of an imaging fluorometer according to the present invention.

FIG. 1 shows an imaging fluorometer, which preferably comprises a source of electromagnetic radiation, optical components to direct the radiation, excitation and emission filters, an imaging device, and a digital computer. In this embodiment, visible light from a single source 21 is used to illuminate (or excite) a sample. Light from this source is first filtered by an excitation filter 23 and then reflected off a mirror 25 oriented so that the reflected light passes through a sample window 26 and impinges on the sample 27. The reflected light excites fluorescence from the sample; this emitted fluorescence passes through an emission filter 29 and lens 31 on its way to an imaging device 33. The collected image is then sent via cables 34 to a digital computer 35 for analysis.

The components of the imaging fluorometer are arranged to promote simple and efficient operation. The excitation light emerges from the lamp 21 substantially perpendicular to the "emission axis" connecting the sample 27 and imaging device 33. (Only fluorescence emitted approximately along the emission axis will be collected by the imaging device.) A single mirror 25 is then sufficient to reflect light onto the sample. This mirror is located so that the excitation light passes through the emission axis before being reflected;

the mirror is oriented so that the reflected light impinges on the sample at an angle only a few degrees off the emission axis. Alternatively, a dichroic mirror could be used to reflect light onto the sample directly along the emission axis. The dichroic mirror would be chosen to reflect the excitation light and transmit the longer-wavelength emission light. Consequently, it could replace or supplement the emission filter 29.

A light source 21 is chosen that emits light with wavelengths suitable for exciting fluorescence from photosynthetic systems. An example is a 500 W, 120-volt projector lamp (model CZX/DAD, GTE Products Inc., is Winchester, Ky.).

Figure 2:
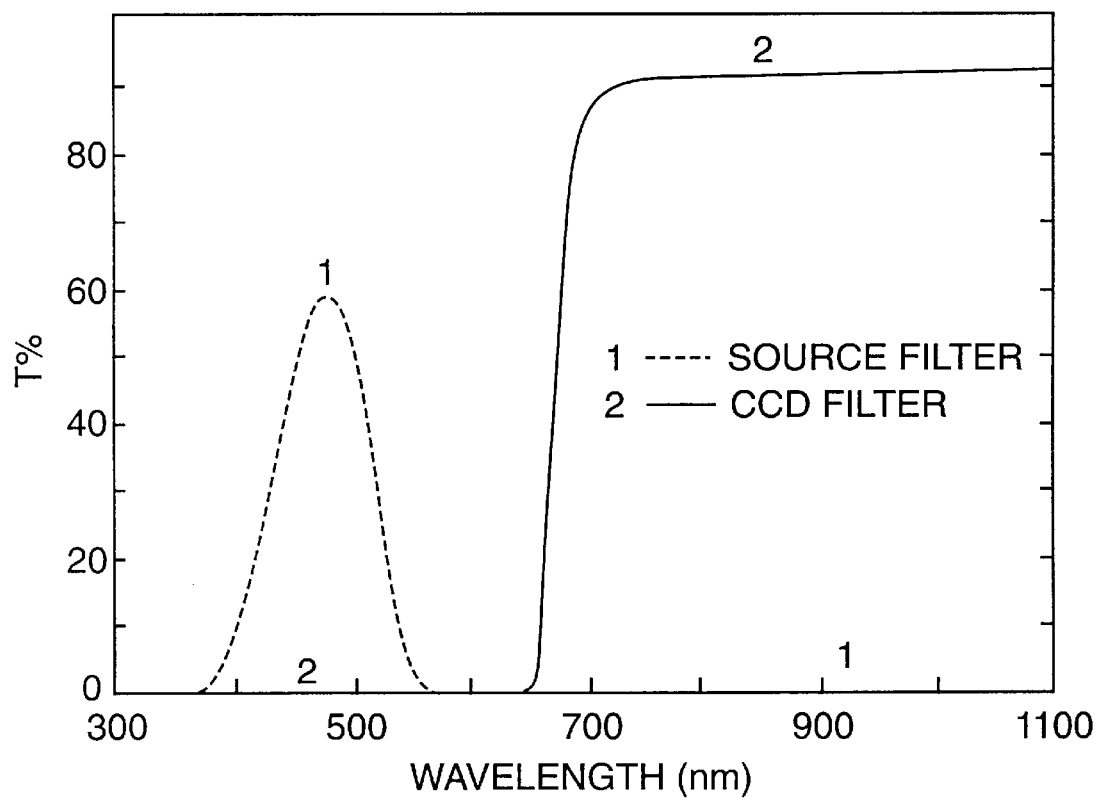
FIG. 2 is a plot of percent transmission versus wavelength for excitation and emission filters used in the imaging fluorometer.

Undesired light is eliminated using filters. The spectral properties of two suitable filters are shown in FIG. 2. On the excitation side, an excitation filter 23 transmits light with wavelengths suited to exciting fluorescence from photosynthetic components. On the emission side, an emission filter 29 blocks the shorter-wavelength scattered excitation light and passes the longer-wavelength fluorescence.

The filtered fluorescence image data are collected by an imaging device 33, such as a charge-coupled device (CCD) camera. A CCD camera is preferred because of its sensitivity and its highly linear response to illumination intensity. An example is a thermoelectrically cooled 12-bit CCD camera (Lynxx PC, CCD Digital Imaging System, Spectra-Source Instruments, Westlake Village, Calif.) with a spatial resolution of 165 by 192 (31,680) pixels.

The digital computer 35 is connected to the imaging device through an interface board and controls the imaging device. Suitable results were obtained using an IBM/PC compatible computer (Pentium chip, 90 MHz, Intel Corp., Palo Alto, Calif.) connected to a CCD camera through a PC interface board (Lynxx PC, Spectra-Source Instruments). However, data acquisition and number of data points could be enhanced by using a faster computer.

Storage of digital images requires considerable system memory. Images may be stored on a hard disk or on removable tapes or cartridges. An example of a suitable storage system is a removable 88 MByte SyQuest cartridge (Model SQ800) on the corresponding internal drive (SyQuest Technology, Fremont, Calif.) for easy access.

Communication with the camera and data analysis may be accomplished using programs developed with suitable software. For example, communication with the camera may be accomplished using a program written in Borland C++3.1 (Borland's International, Scotts Valley Calif. 95067). Data may be retrieved and processed using a numerical software package called MATLAB (The MathWorks, Inc., Natick, Mass.).

Image Acquisition

The imaging fluorometer captures an image of the fluorescence emitted by an illuminated sample containing photosynthetic components. Exposure and total acquisition times depend on the sample and imaging device. For a plant leaf and CCD camera, exposure times are typically about 0.1 s; complete digitization and storage of one image typically takes about 0.6 s using an IBM/PC compatible computer having a 90 MHz Pentium chip. Shorter times can be achieved by using computers with faster processors.

For some applications, a series of images is required, each collected at a defined time. Such acquisition is readily accomplished if the imaging fluorometer is under the control of a digital computer.

Image Analysis

Images obtained at different times may be analyzed individually, or combined to yield images of the effective quantum yield. The effective quantum yield is an empirical estimate of the quantum yield based on several improvements to Eq. 1 made as part of the present invention. First, the need to measure $F_O$, which occurs on the picosecond time scale, is circumvented by replacing $F_O$ with $F_r$. This approximation is generally valid, with some important exceptions, as noted below. Second, the need to obtain an image at the precise time corresponding to $F_P$ is circumvented by obtaining images at a series of times and then approximating $F_P$ by the maximum value $F_m$ obtained in the series. This approximation enables the fluorometer flexibly to handle differences in timing that reflect differences in species, physiology, and pathology. Finally, fluorescence values are corrected, pixel by pixel, for errors introduced by the imaging device. An especially simple correction is to subtract from all fluorescence values the dark signal, $F_{dark}$, obtained in the absence of illumination, although other corrections may also be used.

Combining these three improvements gives an empirical estimate of the quantum yield, denoted Y':

$$Y' \cong (F_m - F_t)/(F_m - F_{dark}) \tag{2}$$

The dark current is not shown in the numerator of Eq. 2 because it cancels out of the difference. Correcting for the dark signal always increases the value of Y', because it always decreases the denominator in Eq. 2.

As a practical matter, the three variables in Eq. 2 are easily measured for each pixel. $F_m$ is defined as the maximum value of the fluorescence obtained from about the first 10 images. $F_t$ is defined as the value of the fluorescence after about 150 seconds, by which time steady-state has been reached. Finally, $F_{dark}$ is defined as the value of the dark signal obtained in the absence of illumination. An image of quantum yield can then be generated by calculating Y' on a pixel-by-pixel basis, using associated values of $F_m$, $F_t$, and $F_{dark}$. A flow chart showing a preferred protocol for calculating Y' is shown in FIG. 3.

Although in this described use the time of $F_m$ is determined for the total leaf image, and not on a pixel-by-pixel basis, the value at that time for each pixel becomes the $F_m$ used in the estimation of Y'. However, since the data set can be considered as in a three dimensional matrix of space and time in the MATLAB program, a variant program was run which calculated time of $F_m$ for each pixel was tested and found to generate equivalent images in healthy leaves.

Values of Y' are typically 0.75–0.85 for healthy dark-adapted leaves; lower values indicate reduced efficiency of energy transfer to the RC or else damaged RC.

EXAMPLE 1—Determination of Fluorescence Transients

Figure 4B:
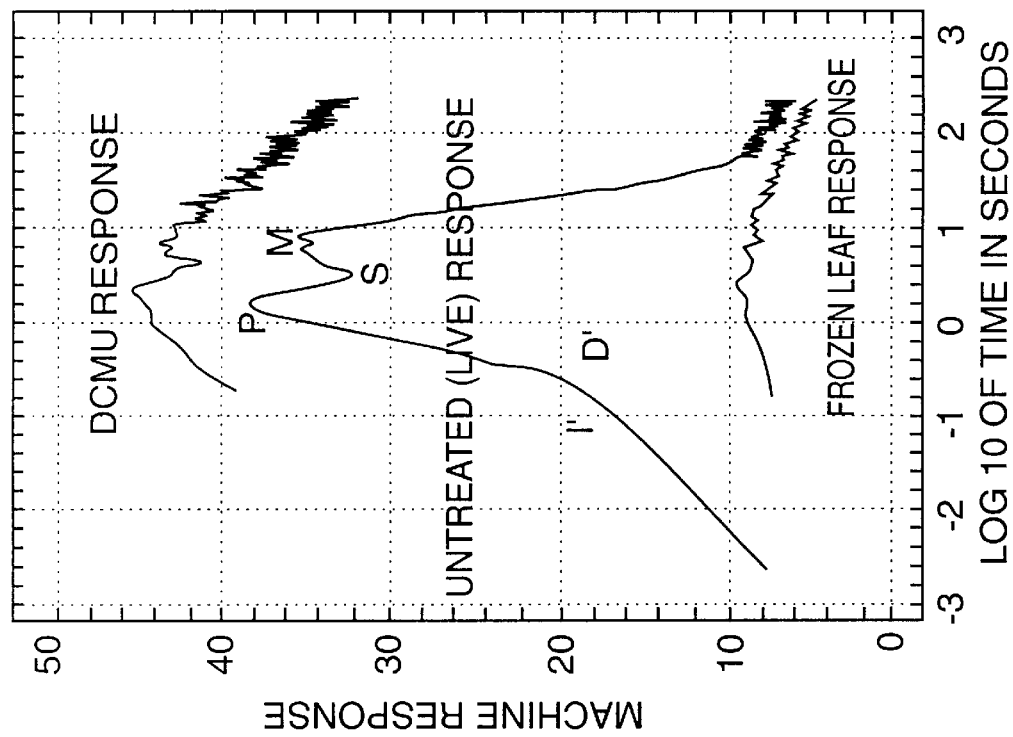
FIGS. 4a and 4b are a plots of fluorescence versus time showing the fluorescence transients obtained upon constant illumination of a dark-adapted leaf from coffee (*Coffee arabica* L.).
Figure 4A:
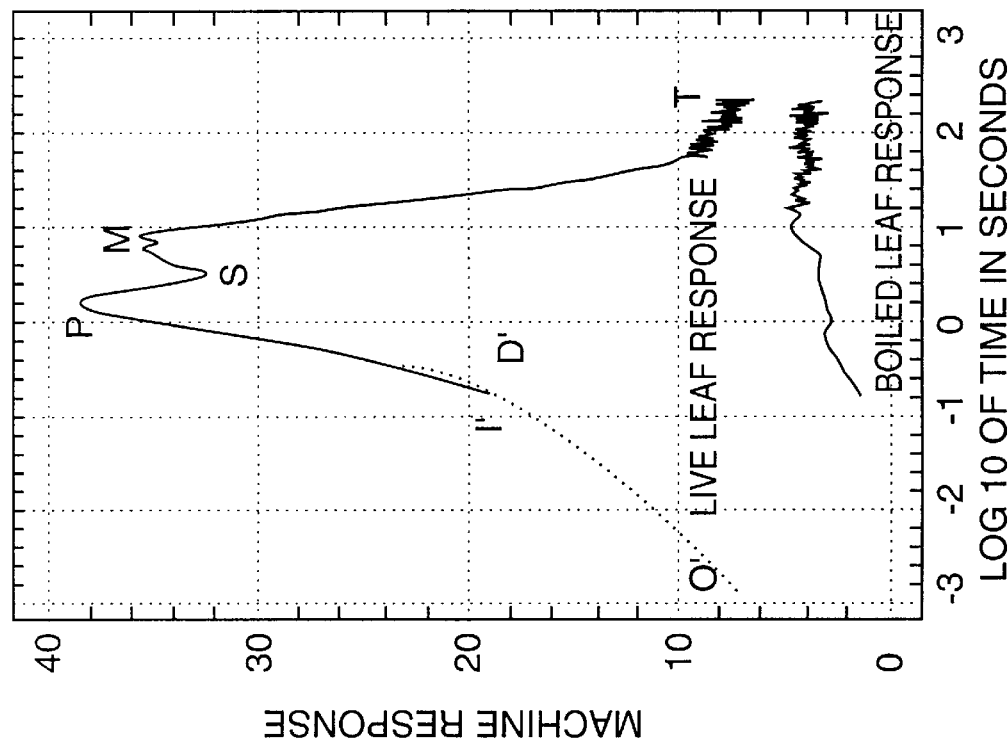

FIGS. 4a and 4b illustrate how the invention can be used to measure the OIDPSMT fluorescence transients that occur when dark-adapted leaves are illuminated. In these figures, data from multiple pixels are combined to give a single fluorescence value at each time point. (In subsequent figures, data from individual pixels are analyzed separately to give images of quantum yield.)

As an example, transients were obtained from coffee (*Coffea arabica* L.) leaves under various conditions. The greatest variation in fluorescence intensity is seen in the untreated (live) leaf, which had been dark-adapted (maintained in an environment with substantially no light in the visually detectable spectrum or near infrared) for 5 hours. Features of interest O', I', D', P, S, M and T are labeled. Transients O, I, and D occur too rapidly to be measured by the imaging fluorometer; they are represented by O', I', and D' in an extrapolated trace. Significantly, values of transients P, S, M, and T measured by the imaging fluorometer are very similar to those measured by point-source fluorescence apparatuses (Karukstis, 1991). Also shown are transients from a) a boiled leaf (FIG. 4a), which had been boiled in water for 25 minutes, b) a frozen leaf (FIG. 4b), which had been frozen with dry ice and then thawed, and c) a DCMU-treated leaf (FIG. 4b), which had been treated with 2 mM DCMU.

The fluorescence transients in FIGS. 4a and 4b were obtained from measurements taken in an area (10 pixels by 10 pixels) near the center of the leaf. Data were collected every 0.1 s; to accelerate data acquisition, the software was modified to run directly under DOS 6.1 (Microsoft Corp., Redmond Wash.), rather than Windows 3.11 (Microsoft Corp.). Subsequent analysis was performed using programs written for MATLAB. The time-dependent fluorescence response was fitted to a Q-spline and then smoothed by a 5-unit "box car" procedure. The Q-spline fit is used because it flexibly responds to complexly varying data. The time-dependent (base-line) CCD response in the absence of the sample was smoothed by fitting to a fifth-order polynomial (Statgraphic-Plus, version 7 for DOS, Manugistics, Inc., Rockville, Md.). About fifty points were used to fit all curves. The traces in FIG. 4 represent the difference between the measured fluorescence and the smoothed base-line response. The data acquisition rate and number of data points can be increased by using the fastest available computer.

EXAMPLE 2—Freeze Damage

Figure 5:
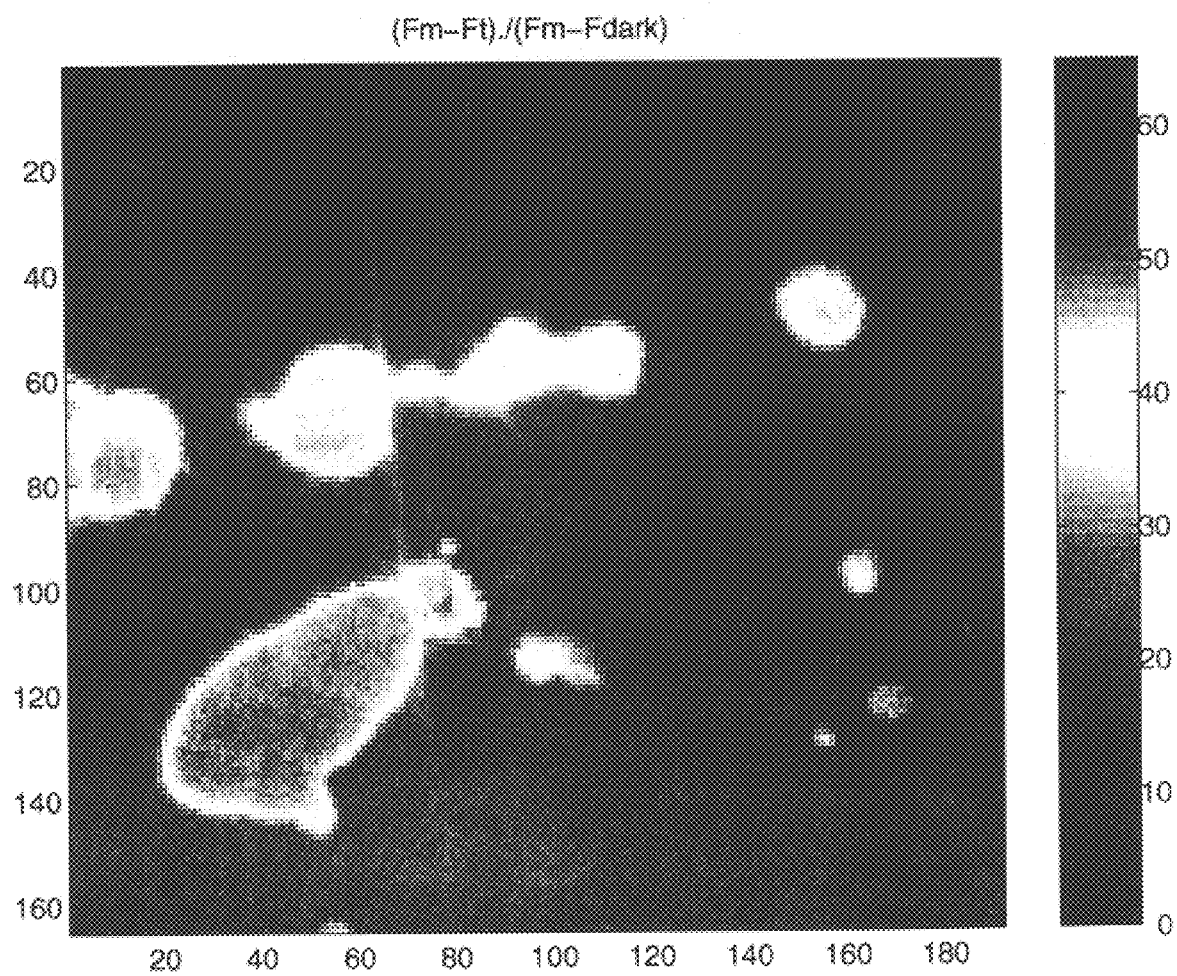
FIG. 5 is an image of the estimated quantum yield Y' showing the effects of freeze damage on a leaf from *Digitalis purpurea* L. The color bar to the right of this and subsequent figures relates color to the value of Y'; the numbers along the ordinate and abscissa are pixel numbers for the digitized image.

FIG. 5 illustrates how the invention may be used to assay freeze damage in plants. Freezing temperatures can damage a leaf's light harvesting systems, leading to nonfunctional RCs and a concomitant decrease in $F_p$ and Y'. In this case, Y' will not equal the maximum intrinsic $PS_{II}$ efficiency; however, it will still reveal damage to the photosynthetic system.

As an example, FIG. 5 shows freeze-damage to leaves from Digitalis purpurea L. To obtain this data, the leaf was first dark-adapted for 15 minutes. Then, while still in the dark, small pieces (about 3 mm diameter) of dry ice were placed directly onto the leaf for 2 minutes, and then removed. Finally, after 5 more minutes in the dark, the leaf was placed in the imaging fluorometer and analyzed.

In the figure, red corresponds to the highest and blue to the lowest values of Y', as indicated by the color bar. The data show that freeze damage is retarded by vascular tissue; in contrast, the DCMU damage in the following example is spread via vascular tissue.

EXAMPLE 3—Herbicide Damage

FIG. 6 illustrates how the invention may be used to detect herbicide damage in plants. Unlike freezing, which inhibits electron flow at the RCs, certain herbicides instead inhibit electron flow beyond the RCs. These herbicides reduce fluorescence quenching, leading to slower fluorescence decay. For example, the herbicide DCMU blocks electron transfer at $Q_B$, preventing re-oxidation of $Q_A$ (Bolhar-Nordenkampf and Oquist, 1993) Consequently, $F_t$ does not decay back to about $F_O$ after the plant is exposed to DCMU; rather $F_t>>F_O$, and $Y'<<Y$. As with freeze damage, Y' will not equal the maximum intrinsic $PS_{II}$ efficiency; however, it will reveal damage to the photosynthetic system. In contrast, Y will not reveal the damage, because it is based on $F_O$, which is unchanged by the herbicide.

Figure 6A:
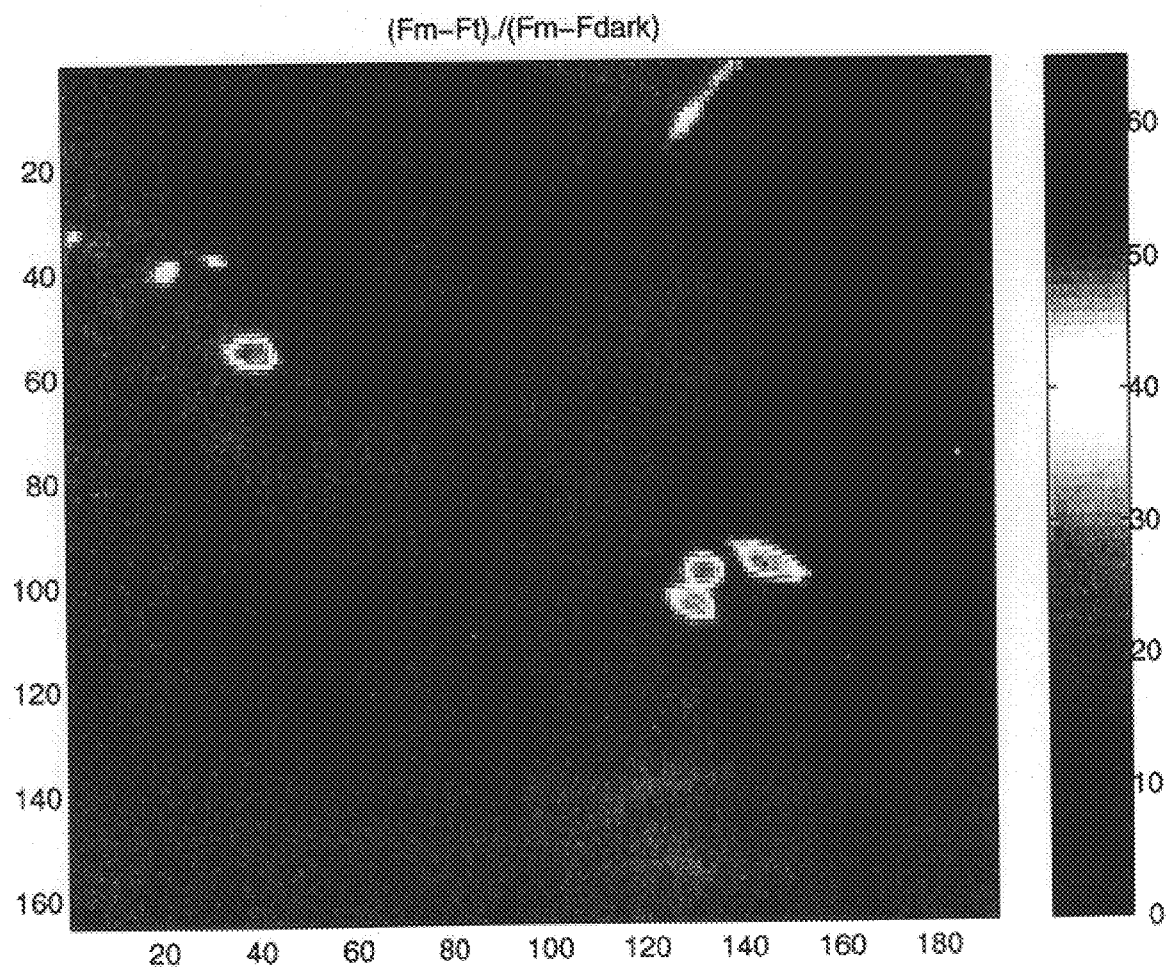
FIGS. 6a and 6b are images of the estimated quantum yield Y' showing the effects of 50 $\mu$M DCMU herbicide on leaves from *Amaranthus cruentus* L.
Figure 6B:
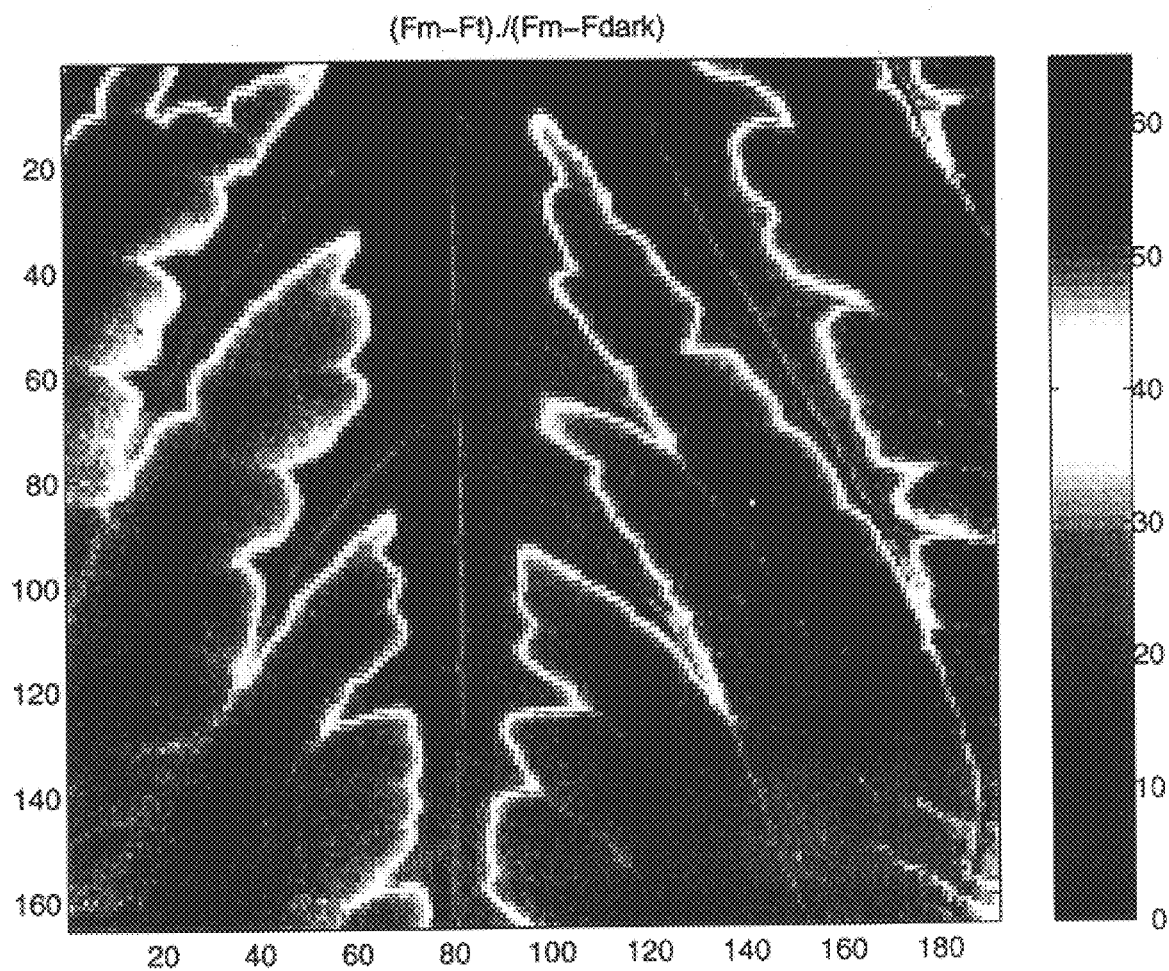

As an example, leaves of Amaranthus cruentus L. were treated with 50 $\mu$M DCMU and then kept in the dark for 15 minutes. FIG. 6a shows effects of a 15-minute exposure to droplets, demonstrating the fluorometer's ability rapidly to detect and localize herbicide damage. FIG. 6b shows the effects 12 hours after allowing the petiole of the leaf to take up the DCMU solution, demonstrating the fluorometer's ability to assess the spread of damage via the vascular tissue of the leaf.

EXAMPLE 4—Disease Damage

Figure 7:
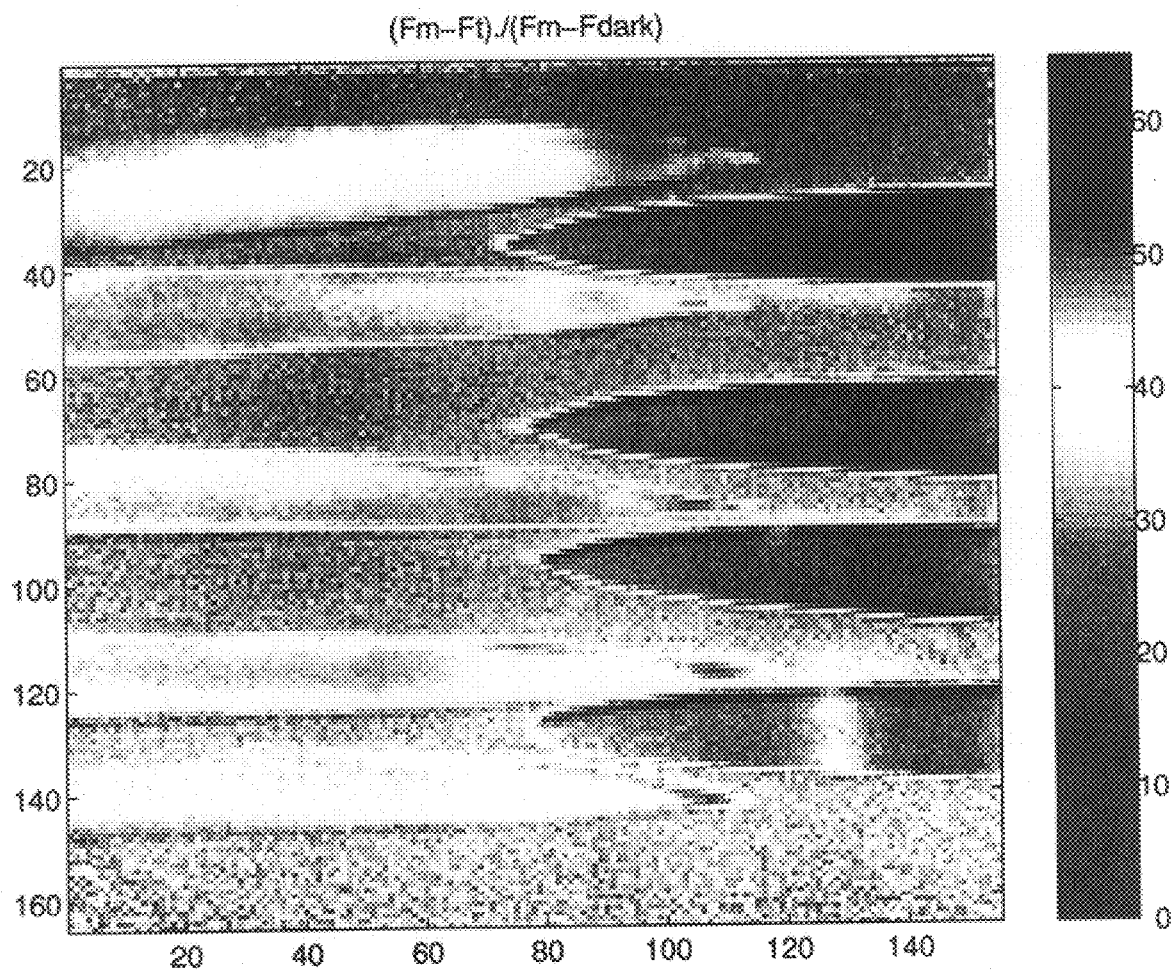
FIG. 7 is an image of the estimated quantum yield Y' showing the effects of the Pestalotiopsis spp. fungal pathogen on needles from the endangered nutmeg cedar or yew (*Rorreya taxifolia* Arn.). Needles on the left were infected by the pathogen, whereas needles on the right were not.

FIG. 7 illustrates how the invention may be used to detect disease damage in plants. As an example, pathogen-free and pathogen-afflicted needles (leaves) were analyzed from the endangered nutmeg cedar or yew (Torreya taxifolia Arn.); needles were dark-adapted for 20 minutes before fluorescence measurements. The yellowish needles on the left clearly reveal toxin-induced damage caused by the fungus Pestalotiopsis spp. Yet, the needles themselves are free of the fungus that has colonized stem tissues at least 10 cm below the needles, and there are no symptoms visible to the human eye. The reddish needles on the right are from a healthy, pathogen-free plant. The slight yellow band on the lowest healthy needle was caused by folding damage during transport.

EXAMPLE 5—Phytotoxin Damage

As another example of using the invention to detect disease-related damage, the effects of isolated fungal toxins on hibiscus were analyzed. Four different toxins—pestaloside, hydroxypestalopyrone, triticone, and pestalopyrone—were applied to three varieties of hibiscus (Hibiscus sabdariffa L.)—non soong, red sorrel, and altissima. The results were strongly dependent on toxin, but independent of hibiscus variety.

Toxins were introduced into leaves by injection, using a 5% ethanol/95% water carrier. Damage caused by the injection itself was corrected for by comparing samples injected with toxins with control samples injected only with the carrier.

Hydroxypestalopyrone and pestaloside did not cause detectable plant damage, even at the highest toxin doses analyzed. Hydroxypestalopyrone is a known phytotoxin in other plant species, but apparently has no effect on hibiscus. Pestaloside is a known anti-microbial agent, which may act on other fungal pathogens to prevent competition without affecting plants.

Triticone and pestalopyrone did cause plant damage. Damage at the highest toxin doses used, 1.4 $\mu$g, was apparent for triticone and pestalopyrone in the image of Y' within 30 minutes after injection. The damage caused by triticone was still obvious after 24 hours. The damage caused by pestalopyrone was no longer apparent several hours after injection, suggesting that the leaf was able to recover rapidly from the damage caused by this toxin.

The dose and time dependence of phytotoxin damage were determined for triticone. A dose of [<] 0.07 $\mu$g caused no damage. A dose of 0.3 $\mu$g caused damage, but only after at least one hour had elapsed; the extent of damage increased for at least 24 hours. Finally, a dose of 1.4 $\mu$g caused damage within 30 minutes; the extent of damage increased for several hours and then remained unchanged.

Imaging was consistently more sensitive than visual inspection. For pestalopyrone, the damage was never visible, even at the highest dose; in contrast, the damage was readily detectable with the fluorometer. For triticone, the damage caused by the highest dose was visible as a light brown ring around the point of injection, but only-after about 5 hours. Thus, for both toxins, fluorescence imaging yielded more rapid and sensitive detection of damage than did visual inspection.

EXAMPLE 6—Remote Sensing

FIG. 8 illustrates how the invention may be adapted to remote-sensing applications, when the leaf is relatively far from the fluorometer. Remote sensing is possible simply by adjusting the light and camera to focus on a distant leaf. Increasing the distance between the apparatus and sample decreases the fluorescence signal; however, this decrease may be offset by using broader excitation and emission filters or a more powerful or more focused light source or laser.

The sample needs to be in the dark before the experiment; consequently, these measurements must be performed at night or in an enclosed space with little or no external light. In other uses, such as to detect the sufficiency or lack of light to a leaf, it is sufficient to keep the leaf in darkness only during the duration of the measurement, that is, without prior dark-adaption.

As an example, the device was used to analyze, from a distance of 7 meters, freeze and herbicide damage in coffee leaves. Three leaves were analyzed. The leaf on the left side of each panel was treated by freezing with dry ice and then thawing; this leaf is barely visible. The leaf in the center was left untreated as a control. The leaf on the right was treated by partially dipping it into 2 mM DCMU.

Figure 8A:
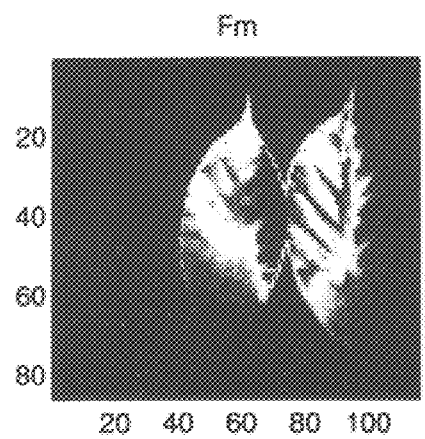
FIGS. 8a–8d are four images showing how data are combined to determine the estimated quantum yield, Y'; data were obtained from coffee leaves imaged from a distance of 7 m. Each panel shows three leaves (from left to right): a) a freeze-damaged leaf (barely visible), b) an untreated control leaf, and c) a DCMU herbicide-damaged leaf, treated by dipping its lower half in 2 mM DCMU.
Figure 8B:
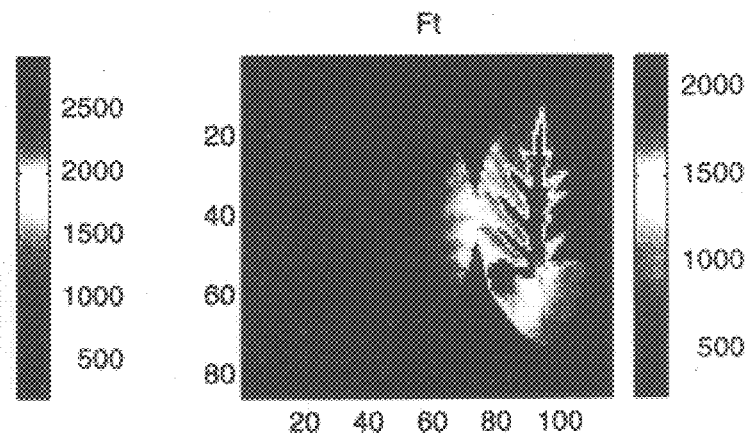
Figure 8C:
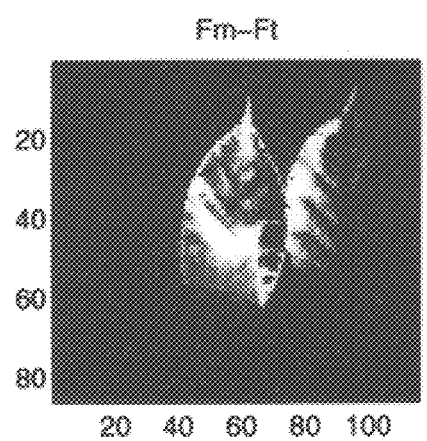
Figure 8D:
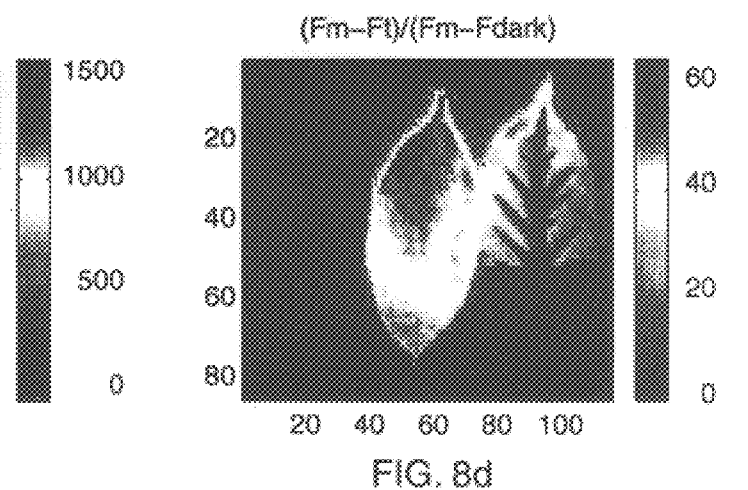

Responses are shown for (FIG. 8a) the maximal fluorescence ($F_m$), (FIG. 8b) the terminal fluorescence ($F_t$), (FIG. 8c) the difference between these two quantities ($F_m$-$F_t$), and (FIG. 8d) the effective quantum yield Y'=($F_m$-$F_t$)/($F_m$-$F_{dark}$). Color bars in FIGS. 8a–8c represent CCD (machine) response. The Y' equation in FIG. 8d is in percent. This format allows comparisons between the strength of signals evaluated in FIGS. 8a–8c.

(a) Maximal transient fluorescence alone is sufficient to distinguish the non-fluorescing freeze-damaged leaf from the untreated and DCMU-treated leaves. However, maximal fluorescence is insufficient to distinguish between the DCMU-treated and control leaves. (b) Terminal fluorescence reveals some differences between the DCMU-treated and control leaves, resulting mostly from the slowing in fluorescence decay induced by the herbicide. However, the area of the DCMU-treated leaf actually treated with DCMU is not delineated. (c) The difference between $F_t$ and $F_m$ distinguishes between all three leaves, but the image of the control leaf is not very uniform. (d) The effective quantum yield (Eq. 2) gives the best results. The frozen leaf is barely visible, the untreated control leaf gives a uniform response, and the DCMU-treated leaf is barely visible in the area that was directly treated and along the vascular tissue of the leaf veins where the DCMU has begun to spread. Thus, the effective quantum yield clearly distinguishes between healthy, freeze-damaged, and DCMU-treated leaves. Second, this process was repeated using four vertical strips. Together, these steps make the lower values, which are the is of the binary code, a uniform blue color. However, the upper values still vary over a range.

The continuous nature of the image was changed to binary using yes/no logic fitted to a threshold. The color range was reduced to two domains: 0s (orange) and is (blue). However, the edges of the rectangles representing the binary code are still ragged, and the effects of leaf venation are still visible.

Although the color or numeric value of the rectangle is not known, the size of the rectangles containing the binary code is known; this size information can be used to smooth the image further. The color of each rectangle is replaced by the color corresponding to the mean of all the pixels of the rectangle. This allows ready machine vision recovery of all 100 encoded digits of π from the original mask.

The technique has revealed considerable variation in the storage abilities of leaves of various species. Moreover, storage abilities can vary with season. Ginkgo leaves no longer produce good images in the fall, even before showing visible signs of senescence. To date, the best leaf source is greenhouse-grown tobacco, which can produce images lasting about eight minutes in vigorous mature leaf tissues.

Although the principles of the present invention are illustrated and described with reference to preferred embodiments, it should be apparent to those of ordinary skill in the art that the illustrated embodiments may be modified in arrangement and detail without departing from such principles. The present invention includes not only the illustrated embodiments, but all such modifications, variations, and equivalents thereof as fall within the true scope and spirit of the following claims.

We claim:

1. A method for assessing differences in pathology and physiology of materials containing photosynthetic components, the method comprising:

illuminating a sample of a material containing photosynthetic components;

measuring fluorescence excited from the sample by the illumination at multiple times to acquire data regarding measured fluorescence as a function of time;

analyzing the data to select a value for the maximum measured fluorescence;

analyzing the data to determine the fluorescence at a fixed time after illumination is begun, the fixed time being after the fluorescence has attained its maximum value; and comparing an indicator for the sample to a standard to determine whether the indicator differs substantially from the standard, a substantial difference indicating that the sample has a pathology or physiology that differs from the pathology or physiology represented by the standard, the indicator comprising the ratio of (a) the difference between the maximum measured fluorescence and the fluorescence at the fixed time after illumination is begun to (b) the maximum measured fluorescence.

2. A method for assessing differences in plant pathology and physiology according to claim 1, the method comprising:

positioning a fluorometer at a location appropriate for measuring fluorescence emitted by a first plant and acquiring data regarding measured fluorescence as a function of time for the first plant; and after measuring the fluorescense of the first plant, moving the fluorometer to a location appropriate for measuring fluorescence emitted by a second plant and acquiring data regarding measured fluorescence as a function of time for the second plant.

3. A method for assessing freeze damage of a plant comprising assessing differences in plant pathology according to the method of claim 1.

4. A method for assessing herbicide damage of a plant comprising assessing differences in plant pathology according to the method of claim 1.

5. A method for assessing disease damage of a plant comprising assessing differences in plant pathology according to the method of claim 1.

6. A method for assessing phytotoxin damage of a plant comprising assessing differences in plant pathology according to the method of claim 1.

7. A method for assessing differences in plant pathology and physiology according to claim 1 wherein the assessing comprises measuring differences induced by variations in plant illumination intensity that occurred during growth of a plant.

8. A method for assessing differences in pathology and physiology according to claim 1 wherein the assessing comprises measuring differences that have been induced by mechanical manipulation of a material containing photosynthetic components.

9. A method for assessing differences in pathology and physiology according to claim 1 wherein the standard is obtained by:

illuminating a healthy sample of the material containing photosynthetic components; and measuring fluorescence excited from the healthy sample to acquire data regarding measured fluorescence as a function of time for the healthy sample, the standard comprising the ratio of (a) the difference between the maximum measured fluorescence and the fluorescence at the fixed time after illumination is begun to (b) the maximum measured fluorescence for the healthy sample.

10. A method for assessing differences in pathology and physiology according to claim 1 wherein the indicator is the effective quantum yield (Y').

11. A method for assessing differences in pathology and physiology according to claim 1 wherein the photosynthetic components comprise chloroplast components.

12. A method for assessing differences in pathology and physiology according to claim 1 wherein the material containing photosynthetic components is plant germplasm.

* * * * *

UNITED STATES PATENT AND TRADEMARK OFFICE
CERTIFICATE OF CORRECTION

PATENT NO.   : 5,981,958
DATED        : November 9, 1999
INVENTOR(S)  : Li et al.

It is certified that error appears in the above-identified patent and that said Letters Patent is hereby corrected as shown below:

Column 1,
Line 6, "Jan. 6, 1996" should read -- Jan. 16, 1996 --.
Line 63, "Dower" should read -- power --.

Column 5,
Line 54, "Lo" should read -- to --.

Column 6,
Line 29, "un" should read -- up --.

Column 7,
Line 12, "Inc., is Winchester" should read -- Inc., Winchester --.

The text at column 11, line 59 to column 12, line 14 should not appear.

Signed and Sealed this

First Day of April, 2003

JAMES E. ROGAN
*Director of the United States Patent and Trademark Office*